US009091656B2

(12) United States Patent
Lee et al.

(10) Patent No.: US 9,091,656 B2
(45) Date of Patent: Jul. 28, 2015

(54) SERS-ACTIVE ABSORBERS FOR THE ANALYSIS OF ANALYTES

(75) Inventors: Seung Joon Lee, Santa Barbara, CA (US); Brian D. Piorek, Santa Barbara, CA (US); Carl D. Meinhart, Santa Barbara, CA (US); Casey Hare, Santa Barbara, CA (US); Norman Douglas Bradley, Santa Barbara, CA (US)

(73) Assignee: OndaVia, Inc., Hayward, CA (US)

( * ) Notice: Subject to any disclaimer, the term of this patent is extended or adjusted under 35 U.S.C. 154(b) by 552 days.

(21) Appl. No.: 13/501,716

(22) PCT Filed: Oct. 14, 2010

(86) PCT No.: PCT/US2010/052742
§ 371 (c)(1),
(2), (4) Date: May 15, 2012

(87) PCT Pub. No.: WO2011/047199
PCT Pub. Date: Apr. 21, 2011

(65) Prior Publication Data
US 2012/0236304 A1 Sep. 20, 2012

Related U.S. Application Data

(60) Provisional application No. 61/251,902, filed on Oct. 15, 2009.

(51) Int. Cl.
*G01J 3/44* (2006.01)
*G01N 21/65* (2006.01)

(52) U.S. Cl.
CPC .................................... *G01N 21/658* (2013.01)

(58) Field of Classification Search
CPC .............................. G01N 21/05; G01N 21/658
See application file for complete search history.

(56) References Cited

U.S. PATENT DOCUMENTS

| 6,614,523 | B1* | 9/2003 | Boss et al. ..................... 356/301 |
| 7,075,642 | B2 | 7/2006 | Koo et al. |
| 7,733,481 | B1* | 6/2010 | Bratkovski et al. ........... 356/301 |
| 2003/0123057 | A1* | 7/2003 | Lemmo et al. ................ 356/301 |
| 2003/0231304 | A1 | 12/2003 | Chan et al. |
| 2005/0031513 | A1* | 2/2005 | McNamara et al. ....... 423/215.5 |
| 2005/0064582 | A1* | 3/2005 | Wittwer et al. ............ 435/287.2 |
| 2005/0282287 | A1 | 12/2005 | Farquharson et al. |
| 2008/0074661 | A1 | 3/2008 | Zhang et al. |
| 2009/0168059 | A1* | 7/2009 | Farquharson et al. ........ 356/301 |
| 2010/0192517 | A1* | 8/2010 | Schach .......................... 53/411 |
| 2011/0020459 | A1* | 1/2011 | Achrol et al. ................. 424/520 |

OTHER PUBLICATIONS

International search report and written opinion dated Jun. 23, 2011 for PCT/US2010/052742.

* cited by examiner

Primary Examiner — Michael A Lyons
Assistant Examiner — Hina F Ayub
(74) Attorney, Agent, or Firm — NUPAT, LLC; Morrison Ulman

(57) ABSTRACT

Solid-type SERS-active substrates (e.g., noble metallic nanostructured powders or noble metallic nanoparticle-coatings on beads, microbeads, particles, etc.) are contained within optically-transparent modules. The modules allow for the controlled introduction of analyte-bearing fluid(s) into SERS-active substrates. The modules also allow for the monitoring of SERS signals emanating from analyte(s) which have accumulated on the confined SERS-active substrates. These SERS signals may be monitored over time by direct readout of the SERS substrates through the optically transparent module for chemical analysis and chemical detection applications.

7 Claims, 6 Drawing Sheets

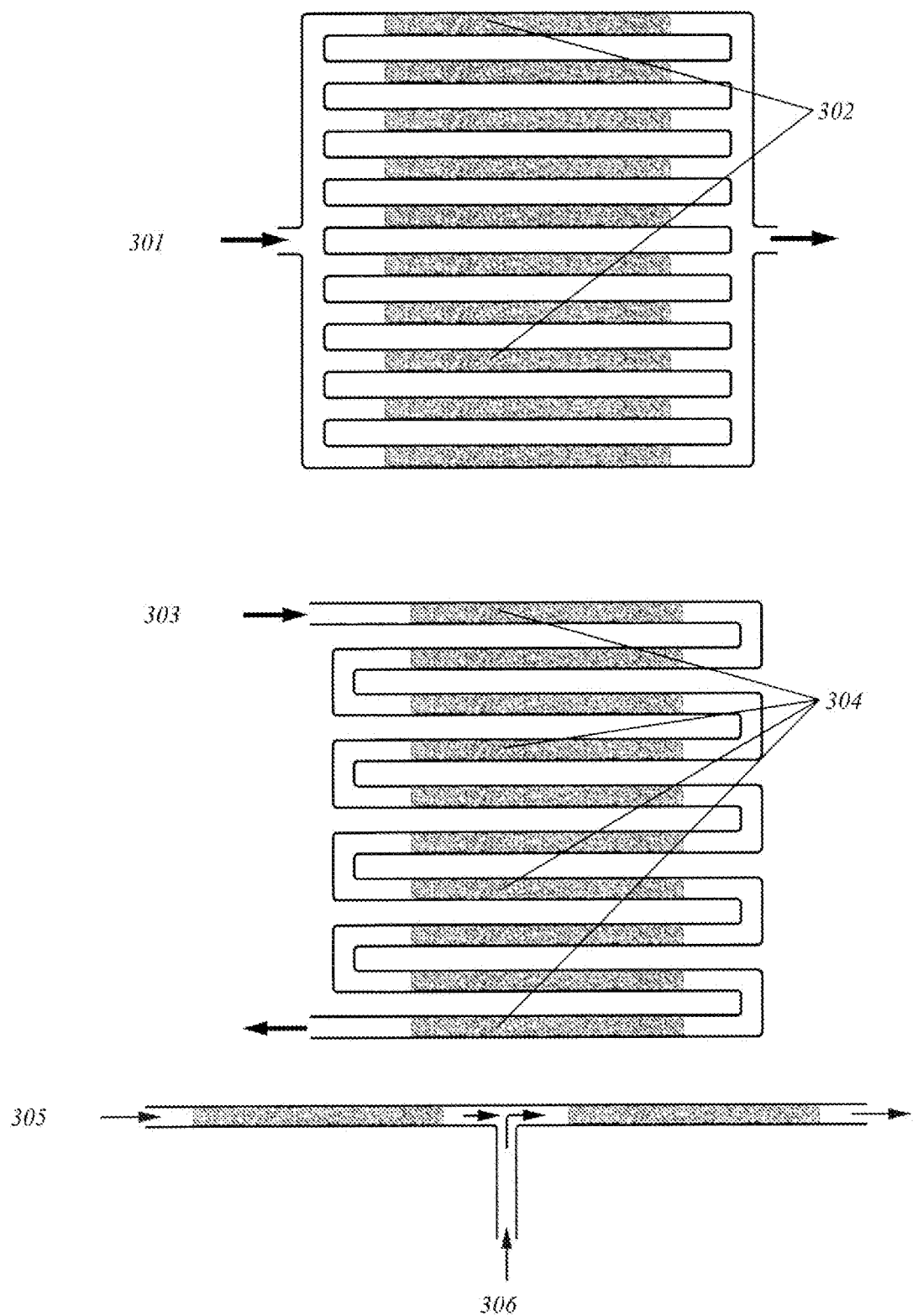

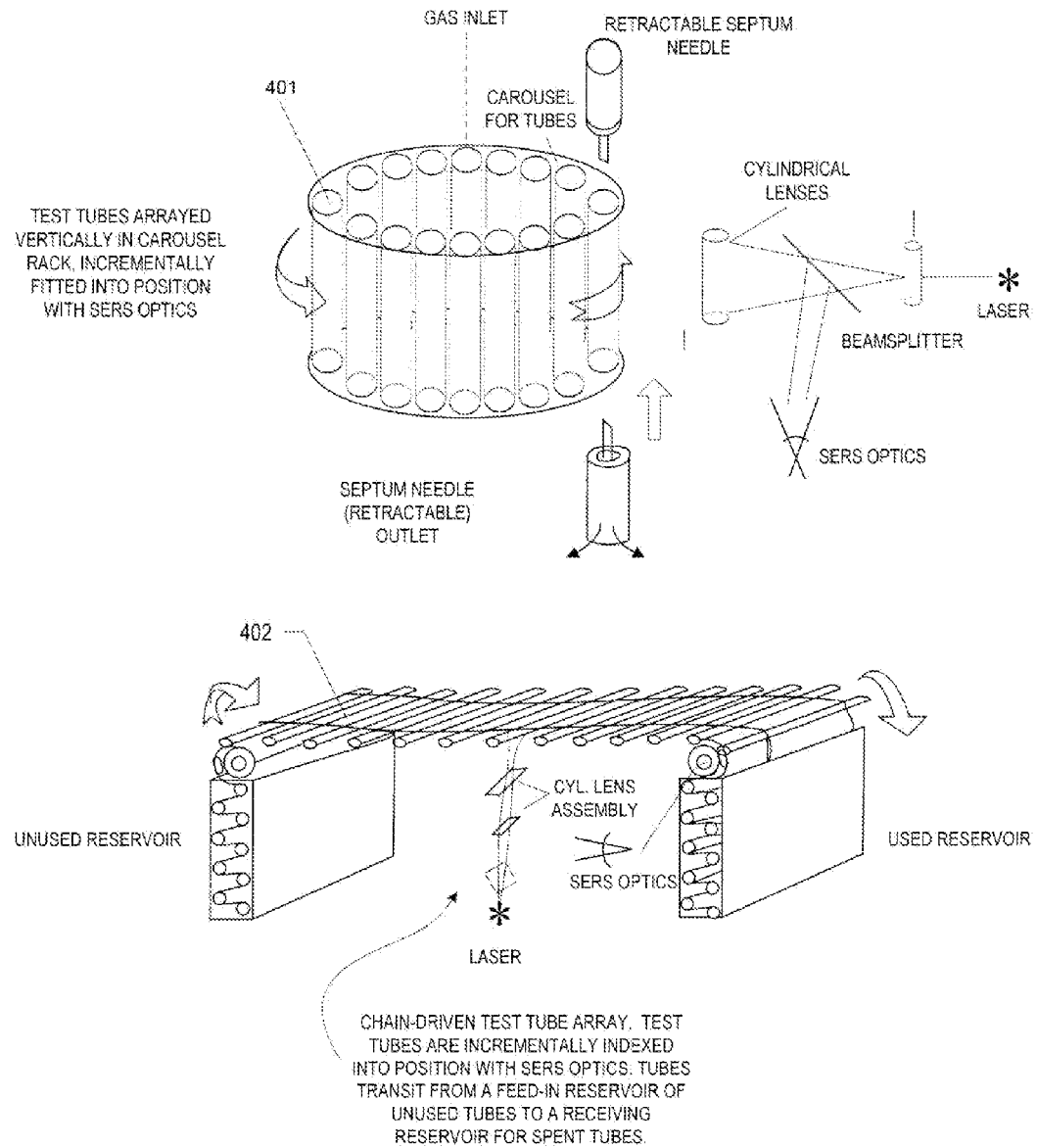

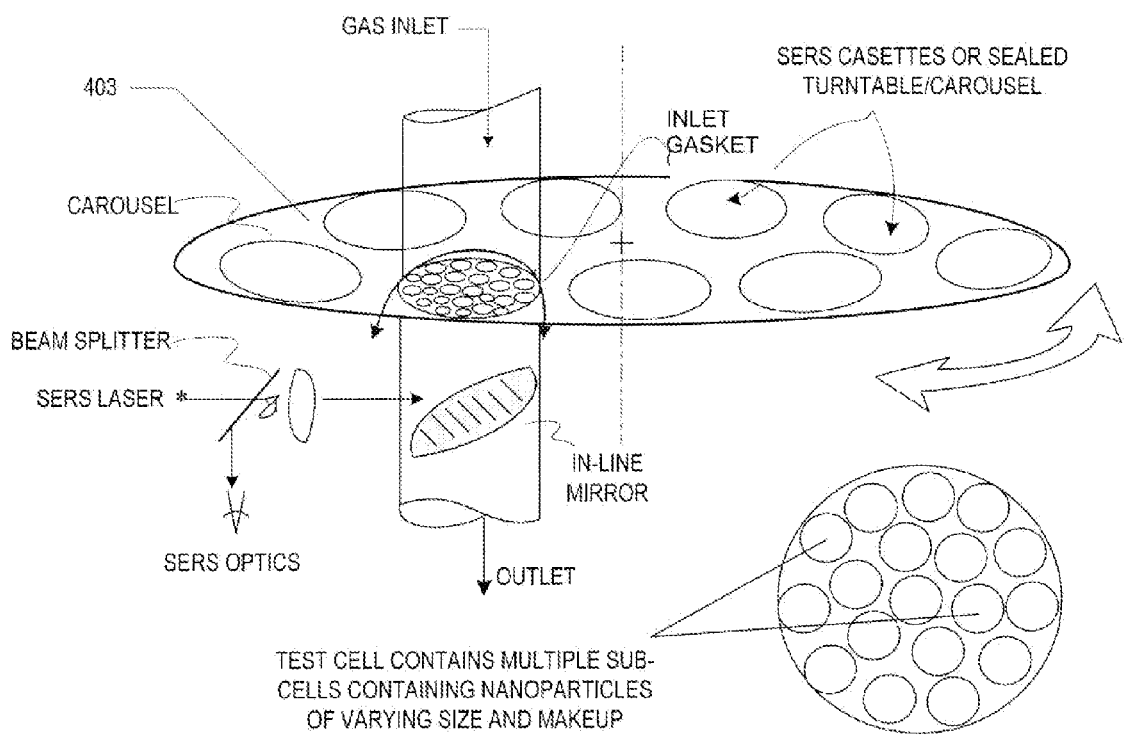

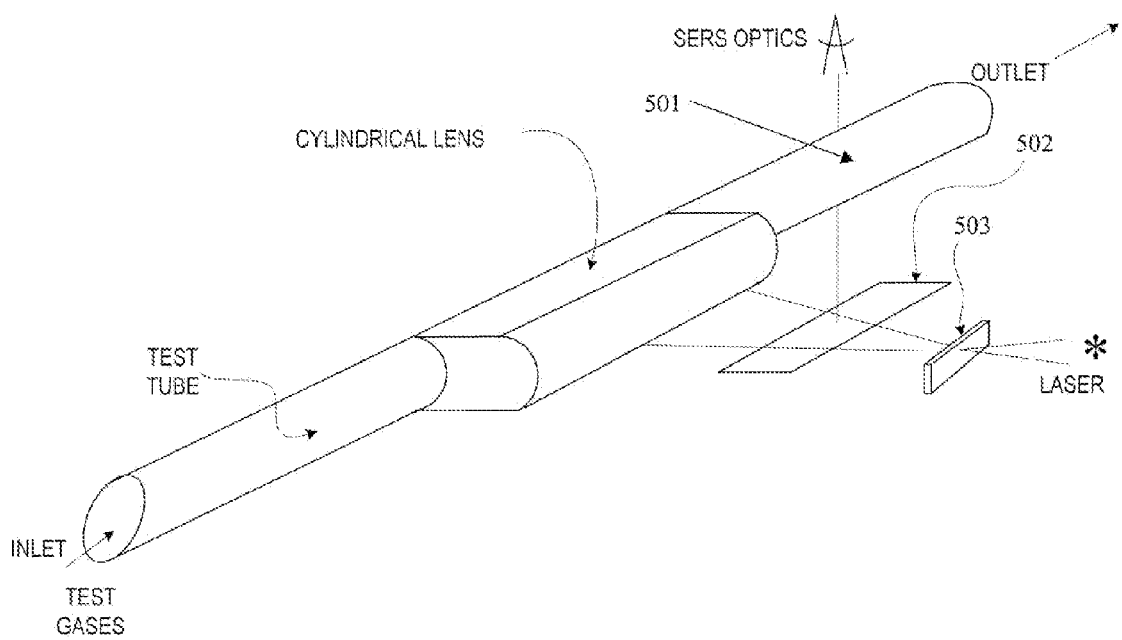

SERS-ACTIVE ABSORBERS FOR THE ANALYSIS OF ANALYTES

RELATED APPLICATION

This patent application is filed pursuant to 35 U.S.C. §371 as a United States National Phase Application of International Application Ser. No. PCT/US10/052742, filed Oct. 14, 2010, which claims the benefit of U.S. Provisional Application Ser. No. 61/251,902, filed Oct. 15, 2009, both of which are incorporated by reference herein in their entirety.

BACKGROUND

Low concentrations of chemical species (analytes) targeted for detection and analysis pose unique technical challenges. Because low-concentration detection and analysis of some chemical compounds necessitate large and heavy lab apparatus, field deployment is often rendered difficult or impossible. In addition, the targeted analytes may be contaminated and/or mixed with false-positive compounds that confound accurate detection and analysis.

By definition, low concentrations generally represent a high ratio of inert or untargeted compounds to the targeted compound(s), often necessitating a process of filtering or other concentration processes, and with or without isolation or removal of contaminants. Thus, preparation is required to isolate and concentrate the analytes prior to the detection/analytic process, also inhibiting field portability.

There is a need for apparatus and processes that are both field portable and accurate, yielding minimal false-positive and false-negative detection events, and offering accurate and repeatable detection/analysis of the targeted analyte(s). Applications include chemical detectors (e.g., hand-held chemical detectors or automated chemical detectors) for low-concentration analytes such as drugs, explosives, chemical and/or biological agents and weapons used in terrorist activities, and biological metabolites.

SUMMARY OF INVENTION

The invention provides systems and processes suitable for analyzing and/or detecting airborne or gas-phase analytes. Various aspects of the invention described herein may be applied to any of the particular applications set forth below or for other types of SERS-based analyte detection devices and systems. The invention may be applied as a stand-alone system or method, or as part of an integrated solution, such as a portable analyte detection system. It shall be understood that different aspects of the invention can be appreciated individually, collectively, or in combination with each other.

In some embodiments, systems or devices described herein include hand-held chemical detectors for low-concentration analytes, such as those derived from drugs, explosives, and biological systems, having enhanced signal stability, accuracy, repeatability, and the ability to spatially locate analyte sources. In other embodiments, systems or dcvi described herein include multiple-module systems, e.g., for use in long-term monitoring. In some embodiments, such multiple module systems comprise an automated configuration to incrementally sample the air. In certain instances, the automated configuration is a timer system, a system based on a triggering mechanism e.g., opening a shipping container door within which the automated system is situated), or the like. In further or alternative embodiments, the multiple module system comprises a configuration to allow manual sampling of the air. Manual configurations may be independently or in combination with automated configurations. In such multiple-module systems, analysis of the sampled air for airborne or gas-phase analytes can be performed utilizing a new or different module of the multiple module system with each sampling.

In certain embodiments, a system suitable for detecting airborne analyte comprises a modular, disposable, interchangeable SERS-active substrate unit which: 1) safeguards against contamination to ensure consistent results; 2) can be stored for long periods of time without performance degradation; 3) can provide long operating time by allowing the automatable swapping of SERS-active substrates to provide renewable SERS-active surfaces which replace contaminated SERS-active surfaces; and/or, 4) may be easily configured for both parallel and serial analysis for detecting multiple chemicals within a mixture.

In certain embodiments, the described SERS-active absorber system utilizes solid-type SERS-active substrate(s) in a module or unit (e.g., comprising a chamber with one or more inlets or inlet structures and, optionally, one or more outlets or outlet structures) having at least one transparent or translucent portion through which the SERS-active substrate and/or analyte deposited thereon can be interrogated. Transparent and/or translucent portions may comprise any transparent or translucent substance (particularly a substantially inert transparent or translucent substance), such as glass, polymer, or the like. In some embodiments, the chamber is a transparent chamber, such as a glass tube. In some embodiments, the module or unit is a glass tube with a septum through which analyte (e.g., in an air sample to be tested) may be inserted into the tube. Solid-type SERS-active substrate(s) may comprise nanostructured noble metallic power(s) (including, e.g., nanoparticles), nanostructured granule(s) of SERS active materials (e.g., noble metallic granule(s), such as nanoparticles or microparticles), nanostructured inorganic beads whose surfaces are coated with a SERS-active material or substrate (e.g., noble metallic nanoparticle(s) or nanostructure(s) or layers), microstructured inorganic beads whose surfaces are coated with a SERS-active material or substrate (e.g., noble metallic nanoparticle(s) or nanostructure(s) or layers), and any other suitable substrate(s). Generally, these particles have a SERS-active surface (i.e., at least a portion of the surface is SERS active), are suitable for packing in a chamber, and, when packed in a chamber, allow a fluid to flow over the substrate and through the chamber (e.g., tube).

In some embodiments, chemicals (e.g., unknown analytes or specifically targeted analytes) which are contained within a fluid (either gaseous or aqueous phases) flow into or through the SERS-active absorber tube and are captured or adsorbed onto the SERS-active surface. In certain embodiments, adsorption onto the SERS-active surface may be achieved through chemical (e.g., electrostatic interaction and/or chemical bonding to the metal surface) and/or physical interaction (e.g., physisorption). For the case of a fluid bearing mixed, multiple chemicals, the flowing operation into or through the SERS-active absorber module can provide wide a stationary phase over which multiple species can be separated and/or sorted along the direction of flow by the resulting chromatographic retardation effect of the solid substrate. In certain instances, this is possible because chemicals have different chemical/physical affinities to the (SERS-active) metal surface(s).

In some embodiments, different analytes may be detected at various points within the chamber as a result of chromatographic retardation of the flow of the analyte-bearing fluid over the SERS-active substrate within the chamber. In certain embodiments, a system described herein is used to determine whether or not a specific analyte of interest is present in a fluid sample (e.g. an airborne or gas phase analyte). In some embodiments, a system described herein may comprise a module configured to determine a likely or known location of the analyte of interest based on the operational parameters of the system, e.g., based on prior experimentation and/or an algorithm, and a system with a Raman spectrometer that may adjust the location of interrogation to the likely or known location of the analyte of interest. Optical stimulation and spectroscopic readout of the SERS-active substrate as a function of distance along the direction of flow by, stimulation with one or more specified wavelengths may provide molecular-specific vibrational Raman signatures of chemicals. Interpretation of these resulting vibrational signatures allow for discrimination of multiple chemicals contained within the mixture, as well as a means for identification and quantification of said chemicals.

Applications include chemical detectors for low-concentration analytes (such as those derived from drugs, explosives, and biological systems) and capable of both short-term, manually operated analysis, and long-term, automated monitoring and analysis.

An aspect of the invention provides microfluidic devices and systems for various applications. Provided in certain embodiments herein is a system suitable for the detection and/or analysis of gas-phase analytes. In certain embodiments, an analyte detection system provided herein comprises:
  a. a plurality of nanostructures (e.g., nanoparticles) comprising a SERS-active surface;
  b. a module comprising a chamber packed with the plurality of nanostructures and comprising at least one transparent or translucent wall portion, and at least one inlet structure;
  c. a device configured to propel a fluid medium through the chamber; and
  d. a Raman spectrometer configured to allow interrogation of the SERS-active surface of one or more of the plurality of nanostructures, or an analyte adsorbed thereon.

In some embodiments, the inlet and/or outlet structures may be a valve, a septum, a narrowed opening, cross-hatched opening (e.g., with openings small enough to keep the nanostructures confined within the chamber), or any other suitable structure for allowing a fluid to flow into and/or out of, including through, the chamber. In some embodiments, the inlet structure may comprise a sealed opening penetrable by an insertion device (e.g., a hypodermic needle), a void into which an analyte bearing fluid is inserted, such as by a hypodermic needle), and a structure for sequestering the SERS-active in the chamber e.g., a cross-hatched structure or a frit). In certain embodiments, the device for propelling the fluid medium through the chamber is a pump, a fan, or any other suitable device.

In some embodiments, the analyte detection system further comprises at least one module configured to chemometrically process at least one output of the analyte detection system. In thriller or alternative embodiments, the system further comprises at least one module configured to adjust one or more variable operating parameters of the system (e.g., flow rate of the fluid into or through the chamber). In specific embodiments, at least one module is configured to adjust one or more variable operating parameters of the system is configured to adjust the one or more variable operating parameters based on the results of the chemometric processing of at least one output of the system.

As analytes interact with and/or are adsorbed onto formed nanostructures within the SERS-active unit, they can be detected and/or analyzed using a variety of technologies. For example, the analytes may be studied using methods such as surface enhanced vibrational spectroscopy, surface plasmon resonance spectroscopy, electrochemical analysis techniques, which may include molecular recognition elements, fluorescent chemical marker techniques, fluorescence quenching, redox-labeled nucleic acid binding techniques (including, but not limited to the molecules DNA, RNA and PNA), X-Ray absorption techniques, IR, visible, UV, and other electromagnetic radiation absorption and spectroscopic techniques, mass spectroscopy techniques, liquid chromatography techniques, flame ionization analysis techniques, DNA melting point techniques, or titration analysis techniques.

Also provided in certain embodiments herein is any SERS-active module described herein. In specific embodiments, the SERS-active module is disposable or recyclable.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The foregoing features and other aspects of the invention are explained in the following description taken in conjunction with the accompanying figures. Further understanding of the features and advantages of the invention will be obtained by reference to the following detailed description that sets forth illustrative embodiments, in which the principles of the invention are utilized.

FIG. 3 illustrates various configurations of modules described herein. In some instances, modules described herein comprise various SERS-active regions comprising SERS-active structures. Such SERS-active regions may be configured in any suitable manner, e.g., in parallel, in series, or the like. Also illustrated in FIG. 3 is a module with a second inlet structure which can be closed or open, e.g., to allow inflow of a second fluid, analyte sample, or the like into the module. In some embodiments, configuration of whether or nut the second inlet is opened or closed at any particular moment may be achieved through chemometric processing.

FIGS. 4A and 4B illustrate various automated configurations of systems described herein.

FIG. 5 illustrates a module having an integrated optical element.

DETAILED DESCRIPTION OF INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Figure 1:
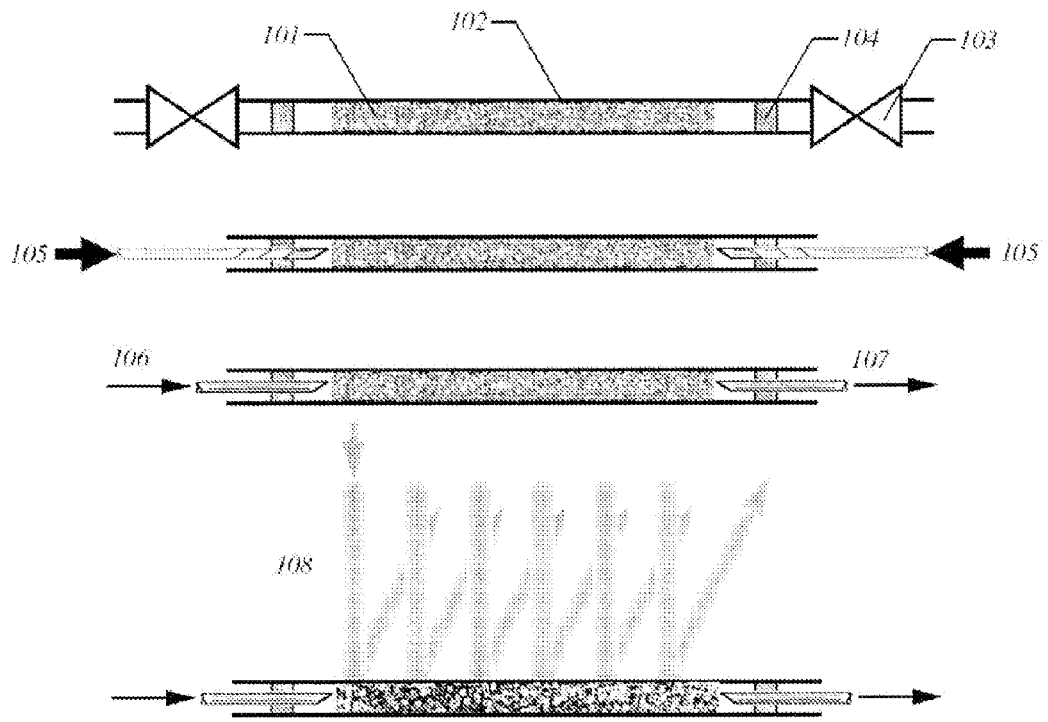
FIG. 1 illustrates a transparent capillary module of a system described herein.

The foregoing features and other aspects of the invention are explained in the following description taken in conjunction with the accompanying figures, wherein:

In one embodiment, a module of a system described herein comprises of a transparent tube or capillary containing SERS-active nanostructure(s). The SERS-active nanostructure(s) include silver or gold nano-/micro-sized powders/granules, silver or gold nanoparticles, coated micro-/nano-sized inorganic particles/powders/granules, and any other suitable substrates that are SERS-active and are able to be packed inside a tube (FIG. 1). For example, the gas-phase chemicals flowing through the SERS-active absorber tube would be adsorbed onto the SERS-active surfaces via chemical (electrostatic interaction and/or chemical bonding to the metal surface) and/or physical interaction (physisorption). A prolonged period of flow provides increasing surface coverage of chemical(s) on the SERS-active nanostructure(s) enabling the recording of vibrational fingerprint(s) by illumination with one or more specified wavelengths. For the multiple chemicals in a mixture, since chemicals have different chemical/physical affinities to the (SERS-active) metal surface(s), the flowing operation through the SERS-active absorber tube can mimic the stationary phase so that multiple species are chromatographically separated and/or sorted along the flowing direction by the resulting chromatographic retardation effect. Optical interrogation as a function of distance along the flowing direction by illumination with one or more specified wavelengths provides molecular specific vibrational Raman signatures of chemicals, thereby allowing discrimination of multiple chemicals out of a mixture. The device can be sealed by valves or gas/fluid-tight septa to safeguard against contamination or premature activation (FIG. 1) and stored under either neutral, positive, or negative pressure (akin to a Vacutainer blood sampling tube). At time of use, the valves are opened or the septa are penetrated (e.g., with hypodermic needles) or valve opened to admit analyte(s) in fluid form at one end, which then flow into or through said capillary.

Figure 2:
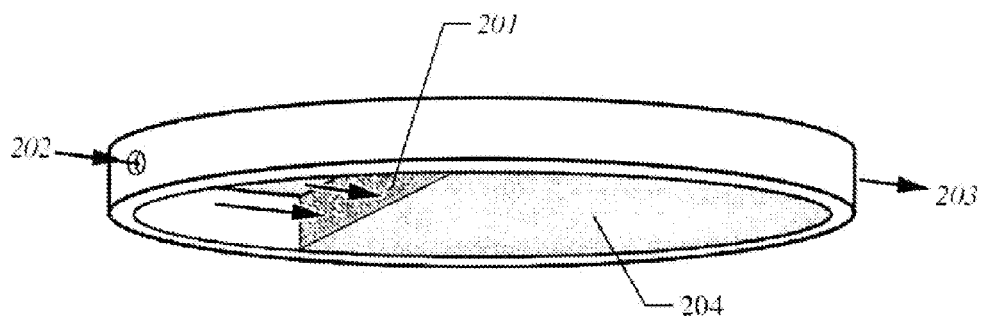
FIG. 2 illustrates a disk-shaped module of a system described herein.

In one embodiment, SERS-active nanostructure(s) (e.g., in powder form) are configured in a transparent, planar (i.e. high aspect ratio) container, such as a disk or plate. In certain instances, this configuration enhances cross-section and exposure to analyte-bearing fluids and affords an enlarged optical interrogation zone. In some embodiments, such modules are also entrained by inlet and/or outlet structures (e.g., valves or gas-tight septa) to safeguard against contamination or premature activation (FIG. 2). At time of use, the inlet and/or outlet structures may be opened (e.g., valves are opened or the septa are penetrated (e.g., with hypodermic needles)) to admit analyte(s) in fluid form. In certain embodiments, wherein an inlet structure and outlet structure are both utilized, the analyte-bearing fluid is admitted into the module chamber at one point, and then flows into (e.g., through an inlet structure) or through said disk or plate and/or is withdrawn from or expelled through a separate point (e.g., an outlet structure). In some instances, the SERS-active absorbers (e.g., SERS-active structures to which analyte is adsorbed) and/or the analytes deposited or adsorbed thereon are optically interrogated through the transparent filter and or gas-tight septa media, typically by illumination at one or more specified wavelengths with subsequent spectral analysis. In certain instances, the disk-shaped module is advantageous because, e.g., the enlarged cross section provides an orthogonal axis which is perpendicular to the bulk flow direction. In some instances, this second axis allows an additional basis of separation over which multiple analytes contained within the flowing fluid can be discriminated. In certain instances, the separation occurring along this axis may be due to physical effects such as the variation of diffusivity of each analyte, the variation of momentum of each analyte, the varying affinity of each analyte to the substrate, and/or the like.

In one embodiment, entrained SERS-active absorber modules or units are plumbed with one or more inlet and outlet points (FIG. 3) to admit analyte-bearing fluid upstream or downstream of segments sensitized to specific analytes and/or which are capable of isolated process controls (e.g., optical interrogation at discrete wavelengths, introduction of polar and/or non-polar solvent(s) vapor, temperature controls, e-fields, etc.). Moreover, valves and gates may be utilized in unison with both manual and automated feedback controls to freely configure parallel and serial segments, for channeling analyte-bearing fluid according to environmental conditions, real-time chromatographic data, and detection results both upstream and downstream of specified segments corresponding to mobile and immobilized phases of the analyte(s).

In one embodiment, a gradient of substrate composition (e.g., a varying radial or longitudinal, distribution of SERS-active nanoparticles by size and/or distribution) exists in the axis perpendicular to the bulk flow direction of the carrier gas fluid. This gradient may then provide additional control of the separation and chromatographic analysis applied to the analyte.

In one embodiment, SERS-active absorber modules or units (e.g., configured as sealed tubes, capillaries, or disks) are stored and deployed within a carousel, turret, rack, or chain, for automated indexing and activation. Depending upon the automated duty cycle, environmental conditions, or manual commands, absorbers are indexed into sampling positions where they are unsealed (e.g., their valves are opened, or their septa are penetrated by hollow needles) and have their contents exposed to an analyte-bearing fluid, then are optically interrogated for detection and analysis (FIG. 4).

Figure 6:
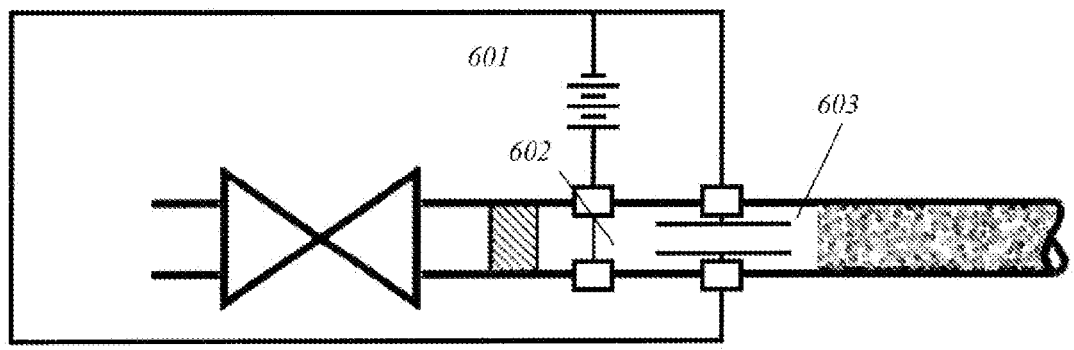
FIG. 6 illustrates integration of electrostatic elements for separation of particulates and/or chemical species flowing into the capillary.

In some embodiments, containment materials used to entrain SERS-active absorbers are designed to facilitate optical functions (e.g., refraction and reflection) useful during interrogation and analysis, including integration with optical sensors and fibers, lenses, mirrors, prisms, shutters, filters, gratings, LEDs, etc. (FIG. 5). In certain JO embodiments, containment materials used to entrain SERS-active absorbers are designed to impart electromagnetic characteristics useful for separating and detecting analytes, including integration of electrostatic and electrolysis contacts, magnetic coils, ion emitters, etc. (FIG. 6). In some embodiments, micron-scale silicates form an active substrate upon which analyte and SERS-active absorbers interact. Nanoroughness and surface area of the SERS-active absorbers may be further enhanced through electrochemical etching. In certain embodiments, a vapor is added to the analyte bearing fluid before injection into a SERS-active absorber module. The quantity of vapor added may be controlled or subjected to a duty cycle such that the vapor density may change within the absorber over time. The vapor may be chosen air its solvation and partitioning properties, such that transfer of analytes within the injected fluid are preferentially transferred onto the surface of the SERS-active material within the module. In some embodiments, Raman imaging/mapping of coupled/arrayed tubes may be performed to enhance performance.

FIG. 1 illustrates one embodiment of the invention wherein a SERS-active material (101) is entrained within a transparent capillary module (102) by gas-tight valves (103) or septa (104). In certain embodiments, an analyte-bearing fluid is introduced at one end of the capillary through a valve or septum (106) and caused to flow into or through the SERS-active material by positive or negative pressure, and/or withdrawn at the opposite end (107). The SERS-active material may be optically interrogated through the all of the capillary for spectral detection and analysis (108). In some embodiments, the inlet and/or outlet structures (e.g., the valves (103) or septa (104) at either end of the capillary) of a module described herein may be closed (i.e., seal the chamber and the SERS-active structures therein) until needed (i.e., until the module is to be utilized). In certain instances, closing of the inlet and/or outlet structures is useful to prevent contamination and premature activation, and to permit long-term storage. At such time as the capillary is used for testing, the inlet and/or outlet structures may be opened (e.g., valves may opened, or the septa are penetrated by hollow needles) to admit and/or withdraw analyte-bearing fluid to and/or from the capillary (105).

FIG. 2 illustrates one embodiment of the invention wherein a test module comprises a SERS-active material (201) (e.g., a plurality of nanostructures with a SERS-active surface) is configured within a planar chamber, such as a disk or plate (cutaway view of SERS-active structures within the disk shown). In certain embodiments, the test module entrains the SERS-active material with a peripheral barrier or wall (e.g., a cylindrical wall) and a top or bottom wall, wherein at least a portion of the peripheral wall, the top wall, and/or bottom wall are transparent. The walls may comprise glass, a transparent film, or a combination thereof. Inlet and/or outlet structures may comprise a valve, a penetrable film (e.g., septum), a seal (e.g., a film), or the like. At time of use, the test module may be unsealed or the inlet and/or outlet structures may otherwise opened to admit (202) and/or withdraw (203) analyte-bearing fluid into and or out of the module. The SERS-active material is optically interrogated through the transparent film (204) for detection and analysis.

FIG. 3 illustrates three configurations of plumbed SERS-active materials, including a parallel array wherein analyte-bearing fluid is admitted to a common manifold (301), then conveyed through a series of test chambers to be optically interrogated singly or collectively (302). In another configuration, SERS-active materials are plumbed as a series of test chambers (303) capable of being optically interrogated singly or collectively (304). Additional plumbing may be employed to introduce agents to a test stream (305) via intermediary channels (306), such as water vapor, molecular recognition agents, and solvents.

In some embodiments, included herein are systems comprising a plurality of modules. In certain embodiments, each of these modules may be single-use modules (e.g., the modules may be disposable or used once and recycled, such as after cleaning or flushing). In some embodiments, analyte-bearing samples may be inserted into an active or "in use" module of one or more such systems. In certain embodiments, a system described herein comprises a module configured to activate or "put in use" a new or second module once analysis within a first module has been completed. The system may then be utilized to detect and/or measure the presence of and/or amount of analyte in a second sample. Such systems may be manual or automated. FIGS. 4A and 4B illustrate three types of automation configurations of systems described herein for indexing sealed testing modules containing SERS-active material, including a turret for tubules (401), a chain-mounted configuration (402), and a rotating carousel for planar-type modules (403). In each configuration, modules are automatically indexed to one or more test positions, where their valves are opened or their septa are penetrated with hollow needles, and analyte-bearing fluid flows into or through the module while the SERS-active material is optically interrogated. At completion of testing, a new module is indexed into the test position.

In some embodiments, a system described herein comprises an optical element to facilitate interrogation of the SERS-active surface or analyte adsorbed thereon. In specific embodiments, the optical element is integrated with a module described herein. FIG. 5 illustrates one type of sealed test module having an integrated optical element (501) in this case a cylindrical lens, to provide a wide-angle optical path for spectral analysis.

Various methods may be utilized to separate different chemicals within an analyte sample. In some embodiments, separation is achieved through fluid chromatographic techniques, electrostatic techniques, and the like. In specific instances, such techniques may involve varying the flow, rate of a fluid, changing the nature of the fluid (e.g., if using air, increasing the humidity thereof), or the like. FIG. 6 illustrates integration of electrostatic elements for separation of particulates and/or chemical species flowing into the capillary. According to certain embodiments of FIG. 6, a charge (601) is applied to incoming, analyte-bearing fluid via a corona wire (602) and grounding electrodes (603), or other electrode configuration, thereby creating an electrostatic separation region.

The invention claimed is:

1. A system comprising:
    a plurality of sealed testing modules automatically indexed to a test position such that when a module is indexed to the test position, analyte-bearing fluid flows through the module for optical SERS interrogation, and at completion of interrogation a new module is indexed into the test position; wherein,
    each module comprises a capillary tube containing SERS-active nanoparticles;
    each module is sealed by an inlet septum and an outlet septum before the module is indexed to the test position; and,
    the septa of a module in the test position are opened to allow fluid flow through the module.

2. The system of claim 1 wherein the plurality of sealed testing modules are indexed by a rotatable carousel.

3. The system of claim 1 wherein the plurality of sealed testing modules are indexed by a chain-driven array that pulls new modules from a feed-in reservoir of unused modules and deposits spent modules in a receiving reservoir for used modules.

4. The system of claim 1, the fluid being in a gas phase.

5. The system of claim 1, the fluid being in a liquid phase.

6. The system of claim 1 wherein the capillary tube comprises an integrated cylindrical lens to facilitate optical SERS interrogation of the SERS-active nanoparticles.

7. The system of claim 1 wherein the septa of a module in the test position are penetrated by retractable hollow needles.

* * * * *